United States Patent [19]

Avrameas et al.

[11] 4,004,979
[45] Jan. 25, 1977

[54] PREPARATION OF ACTIVE PROTEINS CROSS-LINKED TO INACTIVE PROTEINS

[75] Inventors: Stratis Avrameas, La Celle Saint Cloud; Georges Broun, Rouen; Eric Sélégny, Rouen; Daniel Thomas, Rouen, all of France

[73] Assignee: Agence Nationale de Valorisation de la Recherche (ANVAR), Neuilly-sur-Seine, France

[22] Filed: Jan. 15, 1975

[21] Appl. No.: 541,257

Related U.S. Application Data

[63] Continuation of Ser. No. 286,233, Sept. 5, 1972, abandoned, which is a continuation-in-part of Ser. No. 810,835, March 26, 1969, abandoned.

[30] Foreign Application Priority Data

| Mar. 29, 1968 | France | 68.146205 |
|---|---|---|
| Jan. 29, 1969 | France | 69.01451 |
| Mar. 19, 1969 | France | 69.07897 |

[52] U.S. Cl. ................................ 195/68; 195/59; 195/63; 195/DIG. 11; 260/112 R; 424/94
[51] Int. Cl.$^2$ ....................... C07G 7/02; C07G 7/00
[58] Field of Search .............. 195/63, 68, DIG. 11, 195/59; 260/112 R; 424/94

[56] References Cited

UNITED STATES PATENTS

| 3,639,558 | 2/1972 | Csizmas et al. | 195/63 X |
|---|---|---|---|

OTHER PUBLICATIONS

Avrameas et al., Biologically Active Water–Insoluble Protein Polymers, Journal of Biological Chemistry, vol. 242, No. 7, 1967 (pp. 1651–1659).
Silman et al., Some Water–Insoluble Papain Derivatives, Biopolymers, vol. 4, 1966 (pp. 441–448).
Habeeb, A.F.S.A., Preparation of Enzymically Active Water–Insoluble Derivatives of Trypsin, Archives of Biochemistry and Biophysics, vol. 119, 1967 (pp. 264–268).
Goldman et al., Papain Membrane on a Collodion Matrix Science, vol. 150, 1965 (pp. 758–760).

*Primary Examiner*—David M. Naff
*Attorney, Agent, or Firm*—Littlepage, Quaintance, Murphy & Dobyns

[57] ABSTRACT

Articles containing active proteins, such as enzymes, crosslinked to an inactive protein are prepared by dispersing and reacting in a solvent an active protein and an inactive protein simultaneously with a crosslinking agent to crosslink the active and inactive proteins together. The degree of crosslinking can be controlled by introducing tris (hydroxymethyl) aminomethane in an amount sufficient to stop chain growth. Optionally, an inert carrier may be present during crosslinking. The resultant crosslinked active and inactive proteins can be in various forms such as solutions, suspensions, gels, films, membranes, granules, pills or tablets.

3 Claims, No Drawings

PREPARATION OF ACTIVE PROTEINS CROSS-LINKED TO INACTIVE PROTEINS

This application is a continuation of application Ser. No. 286,233, filed Sept. 5, 1972, now abandoned, which, in turn, is a continuation-in-part of application Ser. No. 810,835, filed Mar. 26, 1969, now abandoned.

This invention relates to a process for manufacturing articles containing active protein substances.

More particularly it relates to a new process of cross-linking active proteins together with at least one inactive protein, with or without a preexisting support or carrier.

Among the active proteins the more interesting ones are enzymes.

Enzymes have previously been combined with insoluble supports by the use of adsorption techniques (I. Langmir and V. J. Schaefer, Am. Chem. Soc. 60,1351 (1938)), but the products obtained suffered partial denaturation and the enzymes were progressively freed when they were in contact with substrates. Enzymes attachment was therefore not stable or showed poor resistance to external actions.

Cellulose derivatives and enzymes have been combined by M. A. Mitz and L. J. Sumonaria (Nature, 189,576 (1961)), who, for instance, obtained a carboxymethylcellulose azide from carboxymethylcellulose and then reacted this azide with a stabilized solution of an enzyme.

A similar process is described in J. Epstein and B. Anfinsen's article, J. Biol. Chem., 237, (1962), dealing with a process for coupling carboxymethylcellulose with ribonuclease or trypsin.

In P. Bernfeld et al's article, Science, 142, 678 (1963), a process is described for making antigens and enzymes insoluble by entrapping them into the lattices of synthetical polymers. The process consists in mechanically entrapping soluble macromolecular products into the lattice of a highly cross-linked polymeric material, by polymerizing some synthetical monomers in an aqueous solution in the presence of the biologically active macromolecular substance to be embedded.

Goldman et al. (Biochemistry vol. 7, No. 2, February 1968, pages 486–500) discloses that active Papain-Collodion membranes may be formed by using bis-diazobenzidine-2,2′-disulfonic acid as the cross-linking agent. But it could easily be showed that various other cross-linking agents will not give rise to an active papain containing membrane. Therefore Goldman et al's disclosure is limited to the use of a specific carrier, a specific cross-linking agent and a specific enzyme. Moreover Goldman et al. clearly teaches that bis-diazobenzidine derivatives inactivate the protein to a large extent since too much of it is required to insolubilize the protein.

Hornby et al. (Biochem. J. Vol. 98, 1966, pages 420–424) describes the preparation of ficin chemically attached to CM-celluloses using a method described by Mitz and Summaria. But he describes neither the use of cross-linking agents nor their effect on the activity of the protein active substance.

Moreover several authors described the preparation of water-insoluble derivatives of enzymes:

1. by chemical attachment of the enzyme to a reactive polymer [Bar-Eli, A. & Katchalski, E. Nature, Land. 188,856 (1960) and J. Biol. Chem. 238,1690 (1963) U.S. Pat. No. 3,574,062; Cebra, J. J. et al. J. Biol. Chem. 236,1720 (1961); Levin, Y et al., Biochemistry, 3,1905 (1964); Mitz, M. A. & Summaria, L. J. Nature, Lond. 189,576 (1961); and Manecke, G. Pure appl. Chem. 4, 507 (1962); Habeeb A.F.S.A., Archives of Biochemistry and Biophysics 119, 1967, pages 264–268];

2. by physical adsorption of the enzyme to a charged polymer [Mitz, M. A., Science 123, 1076 (1956); McLaren, A. D. & Estermann, E. F., Arch. Biochem. Biophys. 61,158 (1956); Barnett, L. & Bull, H. Biochem. biophys, Acta, 36,244 (1959); Nikolaev, A. Y. & Mardashev, S. R., Biokhimiya, 26,641 (1961) and Nikolaev, A. Y. Biokhimiya, 27,843 (1962)];

3. by entrapping the enzyme in the insoluble matrix of a cross-linked polymer [Bernfield, P. & Wan, J. Science, 142,678 (1963)]; and 4. by cross-linking of an enzyme by a bifunctional reagent [Habeeb, cited above and Quischo, F. A. & Richards, F. M. Proc. Nat. Acad. Sci. Wash, 52, 833 (1964)], the latter consisting in linking molecules of a pure crystallized enzyme carboxypeptidase, the enzymatic activity being thereby greatly reduced.

These previously known processes have several drawbacks, and among others the following ones:

yields of immobilized active proteins are low, and especially in the case where a carrier with covalent-bindings is used they are strictly dependent on the reactive sites present thereon, the active proteins are not securely attached, the active proteins are denatured during attachment.

It is an object of this invention to provide a process which overcomes the aforesaid drawbacks, and which leads to articles containing active protein substances and wherein a high proportion of the active proteins is attached to a base.

It is a further object of this invention to provide a process for producing articles containing active proteins in which the attachment of said active proteins to a base is stable.

It is a still further object of this invention to provide a process for attaching active proteins to a carrier, in which the active proteins are not denatured during their attachment.

Broadly, the present invention comprises a process according to which active protein substances are cross-linked together with an inactive protein using a cross-linking agent, with or without a preexisting inert carrier.

The process according to the invention more particularly comprises reacting a solution of an active protein substance and an inactive protein substance with a cross-linking agent, in the presence of a carrier, under cross-linking conditions, said active protein substance amounting to about 1 to 20% by weight, preferably 1 to 10% by weight, based on the final weight of the whole proteinic substances, and said cross-linking agent amounting to 0.5 to 8% by weight, preferably to 1 to 2.5% by weight, based on the weight of the whole mixture to be treated, and then removing the unattached molecules and optional drying.

According to one particularly advantageous embodiment of the invention, the carrier itself may be constituted by an inactive protein, more especially by at least one inactive protein which may be coreticulated together with the biologically active protein substance.

It has surprisingly been found that cross-linking of biologically active proteins, such as enzymic molecules, together with an inactive protein, such as human or animal plasma, albumin or plasma proteins, ovalbumin, fibrinogen or hemoglobin, by means of a cross-linking agent, i.e. a bifunctional or polyfunctional agent, eventually in the presence of a suitable carrier, and preferably with the active protein to whole proteinic substance ratios above specified, needs smaller amounts of cross-linking agent and provides higher activity ratios than the previous known techniques wherein no such high amount of inactive proteins was used This process is a considerable simple one which is carried out in one step and can be performed in a short time.

It will be showed hereinafter, cross-linking together with at least one inactive protein according to the invention gives rise to better activity ratios than cross-linking in a carrier but without inactive protein, this having been verified with all the enzymes which were tested by both methods. The activity remaining in the articles obtained according to the invention appeared to be a function of the amount of cross-linking agent: too small amounts of cross-linking agent, i.e. less than 0.5% by weight, cannot result in insolubilization, and the activity shows a maximum for concentrations lower than 8% by weight, a saturation of the active sites appearing at higher rates.

While the present invention is not to be confined to any particular theory, it is believed that the process according to the invention involves a competition of active and inactive proteins for the cross-linking agent, thus restricting the number of amino groups of each molecule to be involved in the cross-linking step. The active proteinic molecules are only slightly modified and few active sites are affected by steric hindrance or by denaturation. Their activity is well preserved, for example in a macromolecular structure where the framework is cross-linked albumin.

Moreover the process according to this invention ensures a homogeneous distribution of the active protein molecules inside the article, thus facilitating the mathematical analysis of such experimental models, for example of membrane behaviour. This process allows the insolubilization of fragile enzymes and scarcely restricts the access of the cofactors or coenzymes. Furthermore cross-linking within a preexisting carrier, such as a membrane, is particularly suitable for various experimental and technical purposes, since said carrier can be selected in accordance with the needs of each experimental or technical condition. The enzymic activity yields of the articles according to this invention range in most cases between 30 and 80% of the activity of the untreated biologically active proteinic substance. Thus even fragile enzyme systems, for instance those using mobile cofactors, can be efficiently immobilized. In case of membrane structures for examples, the activity of the articles bearing enzymes remains unaltered for as long as several months at 4° C.

Many applications of such a process are possible, and consequently numerous applications of it can be carried out. These alternative procedures will be described in greater detail in this specification, where illustrative examples of substrates and active protein substances to which the invention is applied will be given.

Generally speaking, the active protein substances which can be used in the process of this invention may be natural or synthetic products, and they can be used in the crude state or after prior purification. These active protein substances are selected from the group consisting of enzymes, antibodies, antigens, allergens, hormones, microbes and viruses.

The inactive protein substances which can be used in the process of the present invention are human or animal plasma albumin, or plasma proteins, ovalbumin, fibrinogen or hemoglobin, or any mixture thereof.

The active protein and inactive protein containing solutions are usually dissolved in aqueous buffer mediums. The buffers are most frequently inorganic buffers, containing alkaline or alkaline-earth phosphates for example, and are well known to those skilled in the art.

In the process of the invention, any suitable carrier compatible with the active protein substances can be used, that is to say, one that is not liable to denature the said substance. So the article obtained by such a process can be provided with the most varied shapes, as will be seen hereinafter.

The articles can be soluble in an aqueous medium, and therefore be in the form of an aqueous solution, or be suspended in an aqueous medium. The said articles can be gels. They can also be solid masses such as granules, pills, tablets, or a plate, cake or other moulded mass. The carriers used can also provide the article with its final form such as a film membrane or an inert, porous material, for instance. The following macromolecular carriers may be used; cellulose, regenerated cellulose ("Cellophane"), amylose, alginates, dextran, collagen, polyvinyl alcohol, polysilanes, polyacrylamide and their substitution products. The carrier may, further, be an aqueous medium or aqueous solution. Other examples of suitable carriers or supports will become evident from the following detailed description.

As used herein, the term "alginates" is used for salts of a hydrophilic and colloidal hydrocarbon acid extracted from seaweeds which form their cellular walls (or membranes) in the form of a complex of calcium and magnesium.

In this specification, -the term "cross-linking agent" represents any agent chemically capable of combining with at least two molecules of the chemical compounds with which it is brought together. As a general rule, therefore, said cross-linking agents are bifunctional compounds but they may also be polyfunctional compounds. So bodies having multiple, identical or different functions can be used as cross-linking agents, such as: bis dazo benzidines, bis diazoco-anisidine, biepoxides, chloro-5-triazines, diisocyanates, dialdehydes including glutaraldehyde, bismaleimides, ethylchlorocarbonates, carbodiimides.

The process of the invention permits the immobilisation of the molecules of active and/or inactive protein substances, optionally in the presence of a carrier by way of the action of the cross-linking agent.

If the carrier is of the macromolecular type, and is penetrable by the solution of active and inactive protein substances, the molecules of said protein substances are entrapped into the lattice of the carrier. Furthermore, if the carrier possesses functional groups effective to react with the cross-linking agent groups, direct chemical bonds are set up between the carrier and the protein substances which further adds to the solidity of the attachment while in no way modifying the protein substances so attached.

By way of explanation, we shall now give a certain number of examples of embodiments and applications of the process of the invention.

In one application of the process of the invention, an enzyme such as glucose-oxidase, carbonic anhydrase, chymotrypsin is immobilized through a cross-linking agent such as bis diazo o-dianisidine, onto a substrate consisting, for instance, of cellulose, regenerated cellulose such as the material commercially available under the name of "Cellophane", dextran or, a polyvinyl alcohol, the said carriers being in granular or sheet form.

In another application of the process of the invention, an enzyme such as glucose-oxidase is attached by copolymerization to an inert protein, such as albumin, acting as a carrier forming substance, in the presence of a cross-linking agent such as glutaraldehyde. In the same way, an active protein film is prepared by cross-linking albumin and carbonic anhydrase through a bifunctional reactive compound, for example glutaraldehyde. The film so obtained possesses advantageous properties and can, for instance, be used as a biological membrane. Other enzymes can also be incorporated in such a film, bestowing on it the specific properties of the enzyme in question, as in the case with carbonic anhydrase.

In another application of the process of the invention, a film of carbonic anhydrase and an inactive protein substance such as albumin cross-linked with a bifunctional respective compound, e.g. glutaraldehyde, is deposited on the surface of a hydrophobic membrane, and notably a membrane containing silicon. The deposit of this carbonic anhydrase and albumin film on the surface of such a membrane greatly increases the velocity of gas transfer, notably carbon dioxide, through the membrane.

In another application of the process according to the invention, a fabric bearing grafted proteolytic enzymes is manufactured by soaking the initial fabric first in a solution of an hydrolytic enzyme and an inactive protein, then in a solution of a bridging agent, e.g. glutaraldehyde. After rinsing, a fabric is obtained containing enzymes which retain their activity therein.

In another application of the process according to the invention, an active protein such as an enzyme, an antigen or similar protein substance is polymerized in the presence of a bridging agent as well as an inert protein acting as a carrier forming substance and polymerization is stopped so that the article obtained remains soluble in aqueous solvents.

In this case, the active proteins are grafted onto a carrier formed of a water-soluble inactive protein chain.

Glutaraldehyde can be used as a bridging agent.

Plasmatic albumin, for instance, can be used as an inert carrier forming protein substance.

The following active proteins can be incorporated together with an inert protein.

Hydrolytic enzymes, such as the proteolytic, lipolytic and amylolytic hydrolases of the digestive tract, as well as urease, asparaginase and other hydrolytic enzymes; oxidases such as uricase, glucoseoxidase, peroxidase, catalase hydroxylases such as phenylalanine-hydroxylase; isomerases and transferases such as galactose-phosphate uridyl transferase; lyases breaking C-C, C-O and C-N bonds.

Active proteins including soluble antigens and allergens can also be used as in the case of enzymes, these protein fractions having previously been isolated from their natural insoluble substrate.

Such a process can be used for preparing therapeutically active products, in which the availability of the active proteins is improved.

Proteolytic enzymes immobolized in accordance with this process can be administered orally to facilitate or activate digestion.

The enzymes solutions obtained could be administered by intraveneous injection. Certain enzymes, such as uricase and asparaginase, which have a therapeutic effect on gout and acute leukosis respectively, can be injected in this way.

Galactose-phosphate uridyl transferase, as well as phenylalanine hydroxylase can thus be administered in order to permit normal metabolism in the case of subjects who are devoid of the capacity of manufacturing certain enzymes, or who secrete them in insufficient amounts.

The injection of antigens immobilized according to this invention permits the permanent formation of antibodies to be instigated over a long period of time, and that of allergens enables the receiver's organism to be desensitized in a lasting manner.

In all cases, proteins immobilized according to this invention provide delayed action or prolonged therapeutic effects when they are administered, owing to the constitution of the products obtained by such a process.

In one embodiment of the process according to the invention, the active proteins are polymerized, in the presence of a cross-linking agent, with an inactive protein carrier forming substance but without an preexisting support to create a small, insoluble particle such as to be suspended in a physiological or aqueous solution.

The preferred inactive carrier forming protein substance is albumin and the cross-linking agent is for example glutaraldehyde. The active protein molecules effective to be immobilized are selected from the group consisting of enzymes, antigens, antibodies, allergens, microbes, viruses, or other protein substances. The active protein substance can be used in its crude state or after preliminary purification. According to said process, suspensions containing proteolytic enzymes, lyases breaking C-C, C-O and C-N bonds, oxydoreductases, isomerases, transferases or other enzymes can be formed. Furthermore, the process of this invention provides suspensions which can be used therapeutically. Thus, grafted enzymes of a proteolytic lipolytic or amylolytic nature can be administered per se to activate digestion. Suspensions of enzymes such as uricase or asparaginase, for instance, can be administered by subcutaneous, intramuscular or intravenous injection to degrade certain harmful products such as uric acid or to degrade asparagin in some diseases or to make up the chronic insufficiencies found in certain subjects, such as the available amounts of galactose phosphate uridyl transferase found in subjects suffering from galactosemia. Similarly, antigens can be injected subcutaneously to initiate the lasting formation of the corresponding antibodies; likewise, the injection of allergens immobilized onto particles can favorize desensitization to these proteins. Furthermore, it is possible to couple membranes of bacterial origin or whole bacteria to albumin molecules to form particles capable of initiating the formation of antibacterial antibodies in a very lasting manner; similarly, couplings of viruses to inactive proteins, such as albumin, can be effected. These couplings enable effective vaccinations, especially local vaccinations as is the case with rhino-pharyngeal vaccination, or again the supply of germs competing with a disordered intestinal flora.

In another application of the process according to the invention, an active protein is polymerized in the presence of a cross-linking agent and an inactive carrier forming protein unitl a solid and insoluble mass of sufficient size is obtained, said mass containing active proteins which have retained their initial properties. In this case, the active proteins are grafted onto a support of an insoluble protein mass in, for instance, the form of granules, pills or tablets. Many enzymes can so be incorporated into a plasmatic albumin polymer, particularly proteolytic, lypolytic and amylolytic hydrolases; the same holds true for certain microorganisms, which can be linked to albumin molecules by the proteins in their walls. These immoblized proteins and these immobilized microorganisms can be administered per os either to accelerate digestion or to counteract pathological intestinal flora.

In another application of the process according to the invention, there is polymerized, in the presence of a cross-linking agent, at least one enzyme or any other active protein in combination with an inactive protein, within an inert material such as prosthesis, on article used in plastic surgery, etc, having a slight surface porosity permitting the penetration and fixation of said active and inactive proteins. In this case, the active proteins are immobilized into a carrier consisting of a very slightly porous and insoluble inert material.

The use of such treated prostheses, consisting either of a simple protein film, or a film bearing enzymic functions, can be recommended in circumstances where it is desired either to facilitate the covering of prostheses surfaces by neighbouring tissues, or, on the other hand, to prevent such covering. This is particularly the case with prostheses used in plastic surgery, Starr's valve, parts used in osteosynthesis, and all surfaces of insoluble and inert material introduced into the system as a material used in plastic surgery or prostheses.

It will also be noted that the process of the invention provides articles in which the enzymes are immobiized onto a substrate represented by a protein film. After suitable treatment, such films can also be used in cosmetology and therapy.

In such cases, the films obtained by enzyme immobilizing should be dired and sterilized by ultraviolet rays before being packed in sterile containers.

The cutaneous application of such films, or their application to easily accessible mucous, membranes permits the local action of certain enzymes, notably proteolytic enzymes such as trypsin, chymotrypsin, papain, keratinase and elastase, subtilisin, propase, collagenase, pepsin, etc. These enzymes can have a therapeutic effect in certain dermatoses and cicatrization problems.

These enzyme-bearing protein films can also be used in cosmetology for care of the skin.

Apart from the aforesaid applications, the articles obtained by the process according to the invention can be used for active filtration, selective adsorption, electrophoresis, chromatography and other similar applications.

Thus, in the field of active and selective filtration, a solution of proteins can be degraded into the corresponding amino acids and peptides by filtration through a membrane bearing a proteolytic enzyme, such as trypsin, after a treatment according to the process of this invention.

Moreover, in the field of electrophoresis and chromatography, the constants of affinity and transformation of a compound which can be attached by an enzyme can be determined by causing this compound to migrate into an enzyme-bearing film.

The activity yield after cross-linking according to this invention was measured for various enzymes, such as glucose-oxidase, urease, trypsin, catalase, etc.

Some of the procedures are detailed below, but it is well known to one ordinary skilled in the art how to proceed with other enzymes or other biologically active protein substances.

a. Measurement of glucose-oxidase activity

The oxidation of glucose to gluconic acid by glucose-oxidase provides hydrogen peroxide The reaction becomes irreversible after addition of catalase to the protein bearing article.

The activity was measured either by observing the disappearance of glucose or by making use of the pH shift occuring during the reaction. In the first case, the remaining glucose was measured in aliquots, using the method of Hyvarinen and Nikila (Clinica Chimica Acta, 7 142 (1962)). In the second case, the reaction was followed with a pH stat using a 0.015 M glucose solution in 0.005 M phosphate buffer. The predetermined pH was maintained constant by the addition of a 0.1 M sodium hydroxide solution.

b. measurement of urease activity

The hydrolysis of urea into ammonium carbonate was determined either by detecting the appearance of ammonium ions using the well known Berthelot's method therefor, or by using a specific cation electrode.

The formation of ammonium carbonate was also determined with a pH stat using a 0.15 M urea solution in a 0.005 M phosphate buffer. The predetermined pH was maintained constant by the addition of 0.1 M HCl.

c. Measurement of trypsin activity

Degradation of N-benzoyl 1-arginine ethylester (BAEE) was followed by an increased absorption at 253 nm or by the resulting pH shift. As concerns the spectrophotemetric method, a 350 mg/l solution of BAEE was used in a 0.05 M phosphate buffer. Turning now to the pH stat method, the predetermined pH was maintained constant by addition of 0.1 M NaOH.

d. Measurement of catalase activity

The decrease of hydrogen peroxide, initially present at a rate of 0.01 M in a 0.05 M phosphate buffer solution, was observed by its absorption at 240 nm.

The activity yields provided by the articles obtained by the process according to this invention are measured through an enzymic activity ratio $\rho$ (in case where the active protein substances are enzymes), which is defined as:

$$\rho = \frac{\text{activity measured after treatment}}{\text{initial activity in the bulk solution}} \times 100$$

$\rho$ expresses the chemical yield and enzyme activity remaining within the article after the immobilizing treatment according to the invention.

The chemical yield of the immobilization inside the preexisting carrier or after coreticulation with an inactive protein substance is measured by nitrogen titration (in a C.H.N analyzer).

Thus it appeared that, after cross-linking with an inactive protein according to the process of this invention, all of the active proteinic molecules which were introduced were immobilized; the chemical yield was consequently exactly 100%, which means that there were not at all losses in the bath used for the treatment. Moreover the losses by denaturation are very low, since an enzymic yield of more than 80% may be obtained (on the basis of the activity that has been introduced into the bath).

On the other hand, the process according to this invention is not limited to monoenzyme systems; it can also provide sequential enzyme systems or other polyenzymic systems. For example, there can be prepared by this process a structured multilayer bienzymatical membrane comprising two active protein layers and two selective films, the active enzymatical films carrying, respectively, hexokinase and phosphatase coreticulated with an inert protein, e.g. albumin; both are impregnated with ATP and covered on their external side by two selective films permeable to glucose, but impermeable to glucose-6 phosphate.

In this asymmetrical membrane, glucose is temporarily phosphorylated.

The system behaves chemically as a simple ATPase

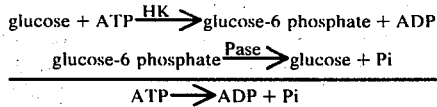

In the first layer, glucose is a substrate and in the second one, glucose is a product.

Whichever form they have, the protein bearing articles according to this invention have an increased resistance towards heat denaturation and proteolysis. The active protein substances keep their activity in a buffer at 25° and 37° C for several months. For instance glucose-oxidase was bound on Cellophane together with albumin according to the invention, by means of glutaraldehyde and kept at 37° C, under dry conditions and in solution. One month later the dry article retained all its initial activity, whereas the solution only retained 60% thereof Under the same conditions, free glucose-oxidase lost all its enzymic activity.

The increased resistance to denaturation and proteolysis of enzymes bound according to this invention was observed with energy enzyme tested. Glucose-oxidase, for instance, was submitted to the effect of trypsin, chymotrypsin and an enzymic preparation commercially available under the name "pronase". Glucose-oxidase which was merely solubilized was inactivated in 5 to 20 hours, whereas glucose-oxidase bound by means of glutaraldehyde in a Cellulose membrane together with fibrinogen according to this invention retained 100% of its activity after at least as long as forty-eight hours.

As regards denaturation by heat, two samples were prepared, the first one (1) consisting in glucose-oxidase bound to Cellophane together with albumin, the second one (2) consisting in glucose-oxidase and albumin coreticulated together according to the invention by means of glutaraldehyde but without any preexisting carrier. The samples were kept at 55° C for various periods of time; the enzymic activity was measured at 25° C, which allowed to consider that denaturation by heat and activation energy were kept separate.

As concerns free enzyme, the activity of free glucose-oxidase decreases down to 50% of its initial value in 6 to 7 hours at 55° C and practically to zero after 40 hours. On the contrary, sample (2) retained more than 90% of its activity after 6–7 hours at 55° C and even about 60% after more than 40 hours at the same temperature; sample (1) retained about 95% of its activity after 6–7 hours at 55° C and about 80% of its activity after more than 40 hours at the same temperature.

Thus, while the present invention is not to be confined to any particular theory, it is believed that two phenomena are involved in the stabilization of the active protein within the articles containing a high proportion of inactive protein and prepared according to this invention:
—insolubilization or gelatinization which stabilizes the proteinic molecular structure;
—local high protein concentration, which has an additional stabilizing effect.

It is to be understood that the active proteins immobilized according to this invention may be used in analytical systems other than those specifically described above; still further, the articles comprising immobilized active proteins of this invention provide a highly advantageous vehicle for the study of the immobilized active protein itself.

This invention is further illustrated by the following examples:

EXAMPLE 1

Several 0.05 mm thick sheets of "Cellophane" Rhone Poulenc's 550 PTOO were 50/50 impregnated with a solution in water of 2 mg/ml of glucose oxidase and 25 mg/ml of a mixture of albumin and fibrinogen for about 5 minutes. They were then dried by ventilation in a cold chamber. The operation was repeated 1 to 5 times to obtain sheets having different activities. The sheets were then impregnated with a 5 mg/ml solution of bis diazo O-dianisidine buffered to pH 6.8 by means of a 0.02 M solution containing 3 parts of monobasic sodium phosphate to one part of dibasic sodium phosphate. The glucose-oxidase molecules which had not been immobilized were removed after the sheets had been passed through several agitated rinsing baths. The sheets were then ready to be used as membranes adapted to many uses.

The enzymic yield, that is the percentage of the activity introduced within the medium which was retained by the final structure, was found to be 65%.

The technique of the preceding examples was repeated using carbonic anhydrase, chymotrypsin and trypsin instead of glucose-oxidase; comparable results were obtained.

Such enzymes were also attached to other carriers such as cellulose, dextrane and polyvinyl alcohol and similar results were obtained.

EXAMPLE 2

25 mg of glucose-oxidase were solubilized in 0.7 ml of phosphate buffer at pH 6.8 and 50 mg of albumin were also solubilized in 0.7 ml of the same buffer. The two solutions were mixed and agitated until a homogeneous mixture was obtained. A solution of 2.5% by weight of glutaraldehyde was added thereto drop by drop with agitation. The solution so obtained was placed in a flat bottomed glass mould at 40 cm² surface. After one hour a 0.1 to 0.2 mm thick film was obtained and was kept in water to prevent it drying out.

The enzymatic yield was found to be 80%.

When a carrier impenetrable to protein solutions and solutions of bridging agents was used, a detachable film was obtained that could be used alone or applied to another carrier.

EXAMPLE 3

3 mg of poorly purified carbonic anhydrase containing about 5% of pure enzyme and 95% of inactive proteins, prepared from ox red blood corpuscles was dissolved in 2 ml of distilled water. To this protein solution there was added 1 ml of a 2.5% glutaraldehyde solution in a 0.02 M phosphate buffer pH 6.8. This mixture is spread on the surface of a hydrophobic silicon memorane commercially available under the name "Silastic 500–3" and manufactured by Dow Corning and Company cross-linking is carried out at 4° C for 12 hours, the solvent was removed by evaporation. A film attached to the membranaceous carrier is obtained. The excess bridging agent was removed by being washed several times in distilled water. The membrane was then rinsed in a 0.022 M veronal buffer solution, pH 7.35.

The enzymic yield was found to be about 30–40% said yield being not easily appreciated, because the methods for the enzymic titrations were in this case not at all precise.

The depositing of a carbonic anhydrase film on such a membrane multiplied by 2 the velocity of transfer of carbon dioxide between two liquids placed on either side of this membrane. This effect is explained by the acceleration of the conversion $CO_3H \rightarrow CO_2 + OH^-$ necessary to pass from the ionized form to the gaseous form of $CO_2$, the only one capable of passing through the "Silastic" membrane, and $CO_2 + OH^- \rightarrow CO_3H$ permitting the solubilization, and therefore the removal of $CO_2$ from the other side of the membrane.

EXAMPLE 4

A solution of 3 mg of purified carbonic anhydrase was mixed in 0.4 ml of 0.02 M phosphate buffer, pH 6.8, with a solution of 50 mg of plasma albumin in 1.4 ml of the same buffer.

1.2 ml of glutaraldehyde at 2.5% in solution in distilled water was added to this solution. Cross-linking took place at 4° C for 12 hours. A continuous, flexible protein film having good mechanical properties was obtained. The molecules which had not reacted were eluated by rinsing with distilled water. The enzymic yield was about 40%, the same remark applying as in example 3.

Such a film, duly rinsed, possesses some of the qualities of biological membranes, notably that of not imparing the figurated elements of blood placed in its contact.

In such a film, other enzymes can be used instead of carbonic anhydrase.

The incorporation of carbonic anhydrase renders this film very permeable to carbon dioxide, permitting its use in oxygenators using membranes.

EXAMPLE 5

In 50 ml of acetic acetate buffer 0.05 M, pH = 5.5 were dissolved sonicated extracts of E. Coli, enriched in glycoproteins by selective acid precipitation. The final proteinic concentration was 5 percent in the bulk solution. Ethylchloroformate was added to a final concentration of 2 percent. The solution was left in a beaker during 10 hours at 20° C. A solid mass appeared. The excess of bifunctional agent was eluated with the above mentioned buffer. The mass was ground and suspended in 90% saline.

These cross-linked extracts are in certain conditions good long lasting antigens. Cross-linking ensures a durable persistance of these antigens in the receptor, for they are uneasily and only slowly degraded in biological media.

EXAMPLE 6

In 50 ml of phosphate buffer 0.1 M, pH = 6.8 containing 8% bovine plasmalbumin (w/v), were suspended washed bacillus subtilis to a final concentration of 50 millions of bacterial bodies per millilitre. Cold glutaraldehyde was added to a concentration of 3 percent. The solution was immediately frozen at −60° C. After 2 hours, the suspension was slowly thawed, giving rise to a lamellar structure containing cross-linked extract of the whole bacterial body. The structure was ground and packed in a column. It degraded amylose and dextrins, as can be shown by the increase of the reducing power and the decrease of coloration in presence of Iodine.

EXAMPLE 7

A suspension of washed penicillium notatum (10 mg per ml of final mixture) in water was added with 2 percent gelatin. To the mixture thoroughly stirred was added slowly and with stirring one volume of 0.1 g/ml of 2,2' disulfonic bisdiazobenzidine for ten volumes of the suspension. The resulting mixture was reacted for 1 hour at 20° C, then spread on a filter paper aerated with a van. The solid obtained by preventilation was then cut and suspended in a phosphate buffer 0.5 M, pH = 7.

The resulting flakes can metabolize glucose, and enable the use of the immobilized microorganisms in continuous flow reactors which can be used for fermentation, therapeutics, and food industries.

EXAMPLE 8

House dust collected and ground was suspended to a concentration of one million particles per ml of phosphate buffer 0.02 M, pH = 6.5 containing 10 mg per ml of human albumin. The mixture was treated by glutaraldehyde at a final concentration of 3% at 15° C for 24 hours. The cake obtained was slowly thawed, then ground and sterilized with ethylene oxide. The same procedure can be used with suspended viruses with substantially similar results.

This procedure allows the realization of allergens which can be used by allergologs. The stabilization obtained favors the preparation of injectable suspensions of cross-linked biological particles controlled in size, and stable for a long time.

EXAMPLE 9

A solution was made containing 150 mg/ml of a protein mixture containing proteolytic and amylolytic enzymes and several inactive proteins and available on the market under the name "Rapidase". 300 ml of this solution impregnate 1 $m^2$ of fabric; the solvent was allowed to evaporate completely at laboratory temperature.

The fabric was then imbided with 300 ml of a glutaraldehyde solution at 2.5%; cross-linking was preferably effected for 1 to 10 hours; the fabric was then well rinsed in distilled water. The enzymic yield was found to be 75% the basis therefor being the degradation of a carbohydrate substrate paving small molecular dimensions (dextrins).

The enzymes introduced into the fabric retained their activity and were notably able for degrading natural substances soaking into the fabric. Soils of blood, sweat, egg were then removed from the fabric simply by rinsing them in water. This action can be explained, without this explanation implying a limitation, by a limited degradation of natural molecules in direct contact with the enzyme-impregnated fabric. The residue of the natural material no longer adhers to the fabric and breaks away in a simple flow of water.

EXAMPLE 10

A solution of 10 mg of glucose-oxidase dissolved with 0.4 ml of 0.02 M phosphate buffer, pH 6.8 was mixed with a solution containing 50 mg plasma albumin in 1.4 ml of the same buffer. 1.2 ml of a 2.5% solution of glutaraldehyde in distilled water was added to this solution. Cross-linking occured after 1 hour at laboratory temperature 0.05 ml of 0.05 M tris (hydroxymethyl-)aminomethane-HCl buffer pH 7.8 was then added to the reaction mixture this having the effect of stopping polymerisation just before the appearance of an insoluble phase. Albumin chains to which two or more molecules of glucose-oxidase attached were thus obtained. The glucose-oxidase retained its activity and specificity. The articles were polymers, as was shown by the measurement of their molecular mass.

The small molecules, such as unreacted glutaraldehyde molecules, were removed by dialysis against 10 volumes of buffer solution, then 10 volumes of water. Each contradialysis liquid was changed hourly, three times over.

The polymer was then freeze-dried; the product was then sterilized with ultra-violet rays and added to an injectable physiological solution the polymer was very stable under rises in temperature and was resistant to most proteolytic enzymes. The enzymic yield was found to be 60%.

Equivalent results were obtained by replacing the glucose-oxidase of the example given above by any enzyme selected from proteolytic, lipolytic and amylolytic hydrolases of the digestive tract, as well as urease, asparaginase and other hydrolytic enzymes; oxidases, such as uricase, peroxidase, catalase; hydroxylases such as phenylalanine-hydroxylase; isomerases and transferases such as galactose-phosphate uridyl transferase; lyases breaking C-C, C-O and C-N bonds, and a soluble antigen or allergen previously freed from its natural insoluble support.

EXAMPLE 11

A solution of 15 mg of α-amylase in 0.4 ml of 0.02M phosphate buffer pH 6.8 was mixed with a solution of 70 mg plasma albumin dissolved in 1.4 ml of the same buffer.

1.2 ml of a solution of glutaraldehyde at 2.5% in distilled water was added to this solution; cross linking took place for 3 hours at laboratory temperature; it was stirred slowly. When an insoluble phase appeared, the degree of insolubilisation was measured by nephelometry. When the phenomenon had reached the desired level, 0.5 ml of 0.05 M buffer tris (hydroxymethyl) aminomethane HCl, pH 7.8 was added, which stopped the polymerization. There was obtained a suspension of polymerized inactive particles formed of albumin, onto which α-amylase molecules were attached these retained their property and specificity. The enzymic yield was found to be 30%, using dextrins as a substrate.

Equivalent results were obtained by replacing the α-amylase used in this example with an enzyme, selected among the proteolytic enzymes, oxido-reductases, lyases breaking C-C, C-O and C-N bonds, isomerases, transferases or other enzymes, and also by an antigen or an allergen.

The fixed, active molecules such as, for instance, enzymes antigens and allergens remained stable by raising the temperature to 50° C and resisted the attack of proteolytic enzymes.

These particles were recovered by filtration on fritted glass, then well washed with the buffer, then with distilled water, until the washing water no longer absorbed light at 280 millimicrons. These particles were then dried, pulverised, sterilised by ultraviolet rays. The powder could then be added to an injectable physiological solution.

EXAMPLE 12

A solution of 11 mg of trypsin in 0.4 ml of 0.02 M phosphate buffer, pH 6.8 was mixed with a solution of 50 mg ovalbumin in 1.4 ml of the same buffer.

1.2 ml of a solution of glutaraldehyde at 2.5% in distilled water was added to this solution. This mixture was placed in moulds of the desired shape; cross-linking occured for 48 hours at laboratory temperature until the material in the mould had completely set. The particles so obtained were removed from the mould and then abundantly rinsed to eluate the the unreacted molecules. The efficiency of the rinsing was checked by light absorption at 280 millimicrons; rinsing is considered as being satisfactory when this absorption is nil. The active molecules attached in this mass retained their activity and specificity. The enzymic yield was found to be 70%, using N-benzoyl 1-arginine ethyl ester.

Equivalent results were obtained by replacing the trypsin in this example by an enzyme selected from the proteolytic, lipolytic and amylolytic hydrolases.

EXAMPLE 13

The surface of a product available on the market under the name of "Cellophane" was used as an inert, insoluble carrier; the surface thereof was impregnated with a solution consisting of a mixture of α-chymotrypsin and inert proteins comprising 20 mg of α-chymotrypsin and 80 mg of inert proteins per ml of 0.02 M phosphate buffer at pH 6.8. The carrier was then sprayed twice with a 2.5% solution of glutaraldehyde in distilled water. Cross-linking took place after 48 hours at laboratory temperature. The product was then well washed, first with the buffer and then with distilled water to remove molecules which had not reacted or were easily detached from the carrier.

The porous surface of the "Cellophane" sheet was thus covered with a thin film of polymerized α-chymotrypsin. The active proteins, bridged to one another or to the inert protein, retained their activity and specificity. The enzymic yield was found to be 50%, using acetly tyrosyl ethyl ester as a substrate.

The product was dried, either by freeze-drying or simply by air at low temperature. Sterilization was carried out with ultra-violet rays. The product could be preserved in sterile bags.

Equivalent results were obtained by replacing the α-chymotrypsin of this example with another enzyme.

in either example 5 or example 8 above, the inactive protein being indicated in parentheses in table I.

TABLE I

| Bound Enzymes | Enzymes efficiently Bound | |
|---|---|---|
| | Yield obtained by immobilization in a Carrier | Yield obtained by coreticulation with an inactive protein |
| Oxido Reductases | | |
| glucose oxidase | 10% on Cellophane | 80% (albumin) |
| urate oxidase | 5% on Cellophane | 30% (albumin) |
| L-amino-acide-oxidase | | 50% (albumin) |
| xanthine oxidase | | 60% (albumin) |
| catalase | 5% on activated carbon | 80% (albumin) |
| peroxidase | 5% on Whatman 3 paper | 60% (albumin) |
| Transferases | | |
| hexokinase | 3% on aminated paper | 30% (albumin) |
| ribonuclease | | 30% (albumin) |
| Isomerases | | |
| glucose-6 phosphate isomerase | | 50% (albumin) |
| triose-phosphate isomerase | | 50% (hemoglobin) |
| Lyases | | |
| carbonic anhydrase | 5% on silicone sheet | |
| tyrosine decarboxylase | | 50% (albumin) |
| phenylalanine decarboxylase | | 60% (albumin) |
| Hydrolases (some examples) | | |
| α-amylase | 2% on silk | 80% (albumin) |
| β-galactosidase | nil(Cellophane) | |
| trypsin | 30% on Cellophane | |
| chymotrypsin | 30% on Cellophane | |
| urease | nil | 60% (albumin) |
| asparaginase | | 30% (albumin) |

EXAMPLE 14

Comparative tests were carried out, the results of wich are shown in table I hereinbelow.

They consisted in testing various enzymes in order to determine the enzymic yield 1) obtained after reticulation of said enzyme in a carrier and 2) obtained after immobilization with an inactive protein according to this invention.

In the first case, the enzyme preparation was fixed onto various insoluble carriers listed in table I. For example, in the case when a sheet of aminated paper was used, it was washed with 0.5 N NaOH, and then water, 0.5 N HCl and water until free of chloride. The wet sheet was washed with acetone and dried then ground. One gramme of dry aminated paper powder was added to 0.5 g enzyme dissolved in 10 ml water; then 0.4 ml of 50% glutaraldehyde was added and the suspension was adjusted to the required pH.

The solution was stirred at room temperature.

After reaction, the suspension was centrifuged and the residue was washed several times with 0.1 M sodium carbonate, water, 0.01 N HCl water until neutral, and was then freeze-dried.

In the second case, the coreticulation was conducted according to the process of this invention as described As it clearly appears from the above table, the process according to this invention always gives unpredictable better results.

What we claim is:

1. A process for producing an article containing a cross-linked active protein substance which comprises dispersing, mixing and reacting in a solvent medium 1. an active protein and 2. an inactive protein simultaneously with 3. a cross-linking agent for said proteins under cross-linking conditions for said cross-linking agent until an active protein substance is formed containing said active protein cross-linked with said inactive protein substance, controlling the degree of cross-linking by introducing tris (hydroxymethyl) aminomethane in an amount sufficient to stop chain growth, said formed active protein substance amounting to about 1 to 20% by weight of the total proteinic substances and said cross-linking agent amounting to about 0.5 to 8% weight based on the weight of the whole mixture being reacted and separating the solvent from said formed active protein substance.

2. The process of claim 1 wherein said cross-linked active protein substance is positioned on a hydrophobic carrier.

3. The process of claim 2 wherein the hydrophobic carrier is a silicone membrane.

* * * * *